(12) United States Patent
Duran

(10) Patent No.: US 7,666,496 B2
(45) Date of Patent: Feb. 23, 2010

(54) MICRO-SINTERED NODE EPTFE STRUCTURE

(75) Inventor: Julio Duran, Morris Plains, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 86 days.

(21) Appl. No.: 11/439,844

(22) Filed: May 24, 2006

(65) Prior Publication Data

US 2007/0276471 A1    Nov. 29, 2007

(51) Int. Cl.
*D21H 13/12* (2006.01)
*B32B 3/26* (2006.01)

(52) U.S. Cl. ............... 428/311.51; 428/315.5; 428/543; 623/1.39; 623/1.49; 623/1.54

(58) Field of Classification Search ............ 428/304.4, 428/311.51, 315.5, 543, 156, 141; 623/1.39, 623/1.49, 1.54
See application file for complete search history.

(56) References Cited

U.S. PATENT DOCUMENTS

| | | | |
|---|---|---|---|
| 5,566,691 A * | 10/1996 | Dolan et al. | 132/321 |
| 5,861,033 A | 1/1999 | Martakos et al. | |
| 5,878,759 A * | 3/1999 | Arias | 132/325 |
| 6,342,294 B1 * | 1/2002 | Ruefer et al. | 428/317.9 |
| 6,780,497 B1 * | 8/2004 | Walter | 428/311.51 |
| 2002/0001704 A1 | 1/2002 | Ruefer et al. | |
| 2004/0122507 A1 | 6/2004 | Henderson | |
| 2005/0153121 A1 | 7/2005 | Ruefer et al. | |
| 2006/0155371 A1 * | 7/2006 | Henderson | 623/1.49 |

FOREIGN PATENT DOCUMENTS

| | | |
|---|---|---|
| WO | WO 01/15633 | 3/2001 |
| WO | WO 02/36332 | 5/2002 |
| WO | WO 2006/074002 | 7/2006 |

OTHER PUBLICATIONS

PCT Notification of Transmittal of the International Search Report and the Written Opinion of the International Searching Authority, or the Declaration for International Application No. PCT/US2007/012340 (2 pages).
PCT International Search Report for International Application No. PCT/US2007/012340 (4 pages).
PCT Written Opinion of the International Searching Authority for International Application No. PCT/US2007/012340 (7 pages).

\* cited by examiner

*Primary Examiner*—Hai Vo
(74) *Attorney, Agent, or Firm*—Vidas Arrett & Steinkraus

(57) ABSTRACT

The ePTFE structure includes an ePTFE structure which has a node and fibril micro-structure. The micro-structure includes specific nodes which are connected to the fibrils. One or more of the specific nodes are sintered and the fibrils are un-sintered. A method for making the ePTFE structure includes identifying and sintering one or more of the specific nodes.

7 Claims, 4 Drawing Sheets

MICRO-SINTERED NODE EPTFE STRUCTURE

FIELD OF THE INVENTION

The present invention relates generally to structures containing expanded polytetrafluoroethylene (ePTFE) and methods for making the same. More specifically, the present invention relates to an ePTFE structures in which one or more nodes of the node and fibril micro-structure thereof are selectively sintered, while leaving other adjacent nodes and fibrils un-sintered. The present invention further relates to a method for making such an ePTFE structure. Such as ePTFE structure may be tubular for use as an endovascular device, such as a vascular graft.

BACKGROUND OF THE INVENTION

It is well known to use extruded tube structures of ePTFE as implantable intraluminal prostheses, particularly as grafts for vascular, esophageal, ureteral and enteral applications. ePTFE is particularly suitable as an implantable prosthesis as it exhibits superior biocompatibility. ePTFE tube structures may be used as vascular grafts in the replacement or repair of a blood vessel as ePTFE exhibits low thrombogenicity. In vascular applications, the grafts are manufactured from ePTFE tube structures which have a microporous microstructure. This micro-structure allows natural tissue ingrowth and cell endothelization once implanted in the vascular system. This contributes to long term healing and patency of the graft. Vascular grafts formed of ePTFE have a fibrous state which is defined by the interspaced nodes interconnected by elongated fibrils.

One disadvantage of current thin-walled or thicker-walled implantable ePTFE tubes is their tendency to kink when subjected to bending forces or concentrated external radial forces. Kinking and luminal constriction can occur during or subsequent to implantation. Such kinking is normally undesirable and poses a risk to the patient.

Accordingly, in applications where kinking is likely, vascular grafts often have an additional support structure to prevent kinking. In some instances, external support structures, such as helical coils, are bonded around the outer surface of the ePTFE tube. Alternatively, individual rings may be bonded to the outer surface of the ePTFE by injection molding.

Such additional support structures have several disadvantages. For example, when the additional support structures are bonded to the outer surface of the ePTFE tube, they increase the outer diameter of the graft in the regions of the support structures. As a result, endoluminal implantation of the graft can be more difficult, such as, for example, when tunneling through tissue is required to implant the graft.

Another disadvantage of grafts having added support structures is that they are often made from materials which are different from the material of the graft wall and require added processing steps such as heat bonding or additional materials such as adhesive to adhere the support structure to the graft. Differential shrinkage or expansion of the external support structure relative to the ePTFE tube can cause the bond to weaken and/or the graft to twist significantly. Separation of the support structure from the graft is obviously undesirable. Additionally, twisting will normally distort the printed linear guideline which typically runs the length of the ePTFE tube and is used by practitioners to determine proper graft disposition to prevent implantation in a twisted configuration. Such distortion may result in the normally longitudinally linear guideline becoming helical or some other non-linear shape prior to implantation of the vascular graft in the patient, thereby defeating the purpose of the guideline.

Other ePTFE grafts have included external polymeric ribs which provide radial support to the lumen, but increase the outer diameter and wall thickness of the graft.

Thus, there is a need for PTFE tubes which are kink resistant without added support structures such as coils or rings and which do not increase the tube outer diameter.

SUMMARY OF THE INVENTION

The ePTFE structure of the present invention has a node and fibril micro-structure. The micro-structure includes specific nodes which are connected to the fibrils. In one embodiment, one or more of the specific nodes are sintered and the fibrils are un-sintered.

In another embodiment, the ePTFE tubular structure may include one or more sintered nodes connected by fibrils at least a portion of which are un-sintered.

In another embodiment, the ePTFE tubular structure may include one or more sintered nodes, and one or more un-sintered nodes connected by fibrils at least a portion of which are un-sintered.

The sintered nodes strengthen the regions of the ePTFE structure in which the sintered nodes are located. The un-sintered nodes and fibrils may provide pliability to the regions of the ePTFE structure in which the un-sintered nodes and fibrils are located.

The ePTFE structure may be formed into a tube structure which, in turn, may be used as an endoluminal graft, such as a vascular graft. Such grafts have several advantages. The selectively sintered nodes provide structural support to the PTFE tube structure to resist kinking thereof. Such structural support is beneficial for thin-walled and thicker-walled PTFE tube structures, and is especially beneficial for thin-walled PTFE tube structures. Also, the sintered nodes do not extend radially beyond the outer surface of the PTFE tube structure so as to not result in an increase in the outer diameter of the tube structure in the regions of the sintered nodes.

Further, the integral relation of the sintered nodes to the PTFE tube structure, i.e., the sintered nodes are part of the PTFE tube structure which has a uniform material, normally eliminates the possibility of differential shrinkage or expansion of the sintered nodes relative to the other portions of the PTFE tube structure. This greatly reduces the possibility of twisting of the PTFE tube structure, and the associated distortion of the guideline prior to insertion of the vascular graft into the patient, which may result from such twisting. The integral relation of the sintered nodes to the PTFE tube structure normally eliminates the possibility of the sintered nodes becoming detached from the PTFE tube structure.

In one embodiment, there is provided a method of making the ePTFE structure which includes selectively sintering one or more of the specific nodes, while leaving other specific nodes and the fibrils are un-sintered.

These and other features of the invention will be more fully understood from the following description of specific embodiments of the invention taken together with the accompanying drawings.

BRIEF DESCRIPTION OF THE DRAWINGS

In the drawings.

Corresponding reference characters indicate corresponding parts throughout the several views of the drawings.

DETAILED DESCRIPTION OF THE INVENTION

Figure 1:
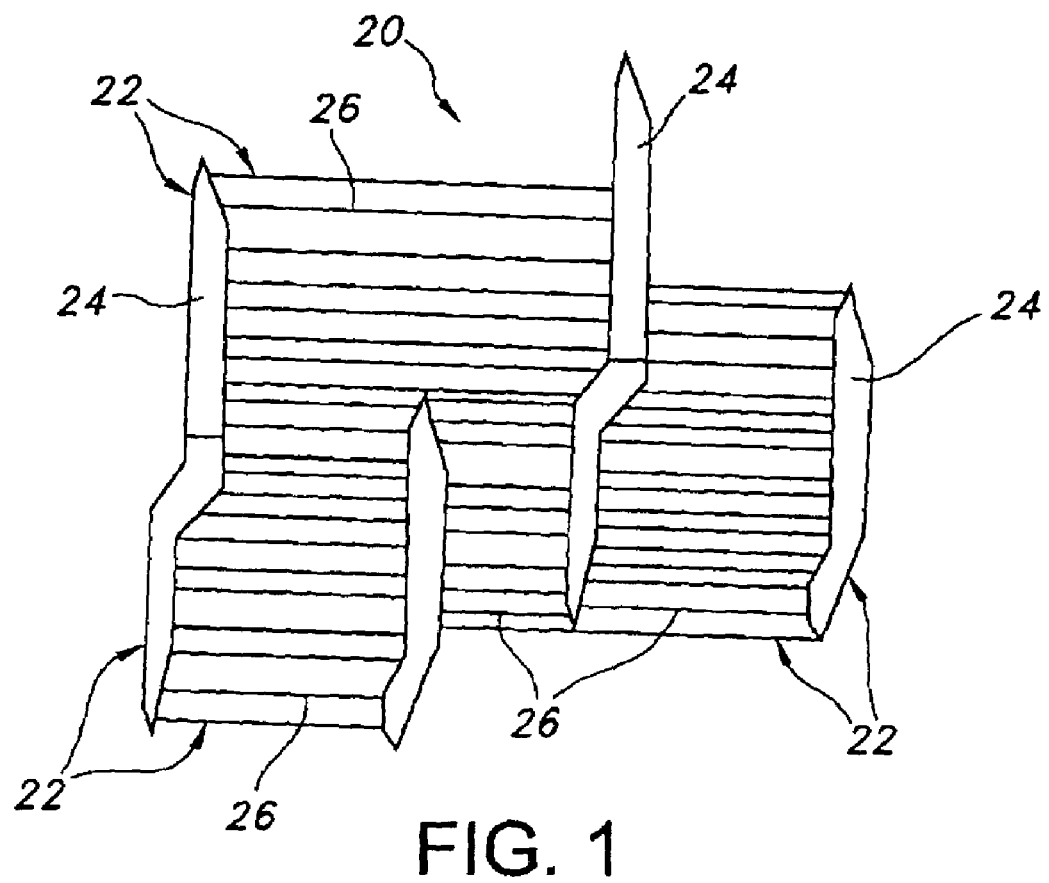
FIG. 1 is a schematic view of a node and fibril micro-structure of an ePTFE structure in accordance with an embodiment of the present invention.

Referring to the drawings and more particularly to FIG. 1, an ePTFE structure 20 includes PTFE which has been expanded. Such PTFE has a node and fibril micro-structure 22 which is defined by interspaced nodes 24 interconnected by elongated fibrils 26. Typically, the orientation of the nodes 24 is transverse relative to the direction of expansion. Also, typically, the orientation of the fibrils 26 is generally the same as the direction of expansion. Each of the nodes 24 of FIG. 1 are connected to many fibrils 26. It may be possible for one or more of the nodes 24 to be connected to as few as a single fibril 26. It is further possible for one or more pairs of nodes 24 to be connected to one another by as few as a single fibril 26. Also, it is possible for individual nodes to be connected directly to one another, as shown in FIG. 1.

Figure 2:
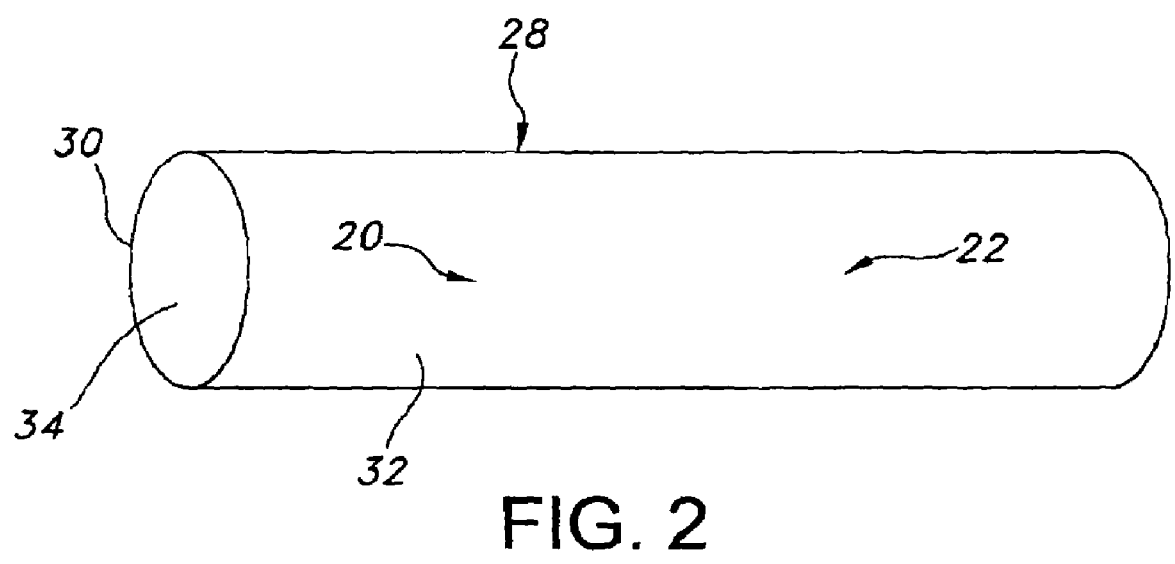
FIG. 2 is a perspective view of a tube structure formed of the ePTFE structure of FIG. 1.

The ePTFE structure 20 may be formed into a tube structure 28, which has outer and inner wall surfaces 32, 34, as shown in FIG. 2. The tube structure 28 may be longitudinally expanded, radially expanded or a combination thereof. Longitudinal expansion of the tube structure 28 will normally produce a node and fibril micro-structure 22, as shown in FIG. 1, in which the fibrils 26 have a longitudinal or parallel orientation relative to the longitudinal axis of the tube structure 28. Radial expansion of the tube structure 28 will normally result in the nodes 24 having a longitudinal or parallel orientation relative to the longitudinal axis of the tube structure 28. Such radial expansion will also typically result in the fibrils 26 having a transverse orientation relative to the longitudinal axis of the tube structure 28.

Multi-axial expansion, i.e., expansion in several directions, may produce a node and fibril structure which has a substantially random pattern of nodes connected by fibrils. In such instances, the nodes and fibrils are often not oriented substantially in either the longitudinal or the radial directions, but are intermediate therebetween.

Figure 3:
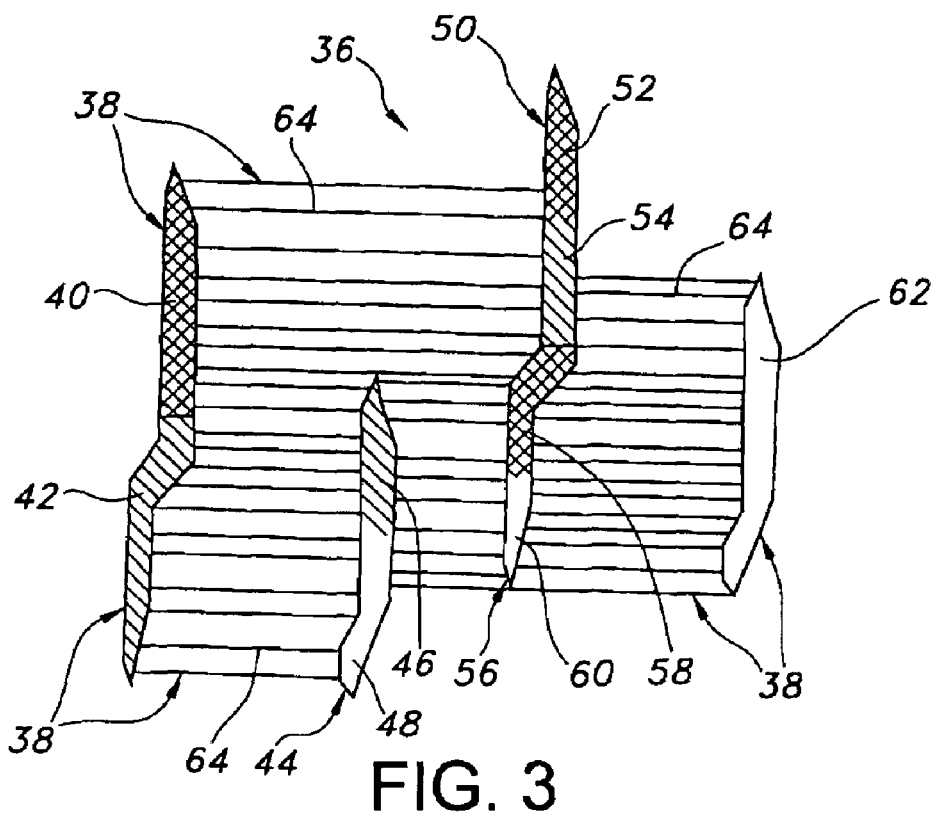
FIG. 3 is a schematic view of the node and fibril microstructure of the ePTFE structure of FIG. 1 after the micro-sintering in accordance with an embodiment of the present invention.
Figure 4:
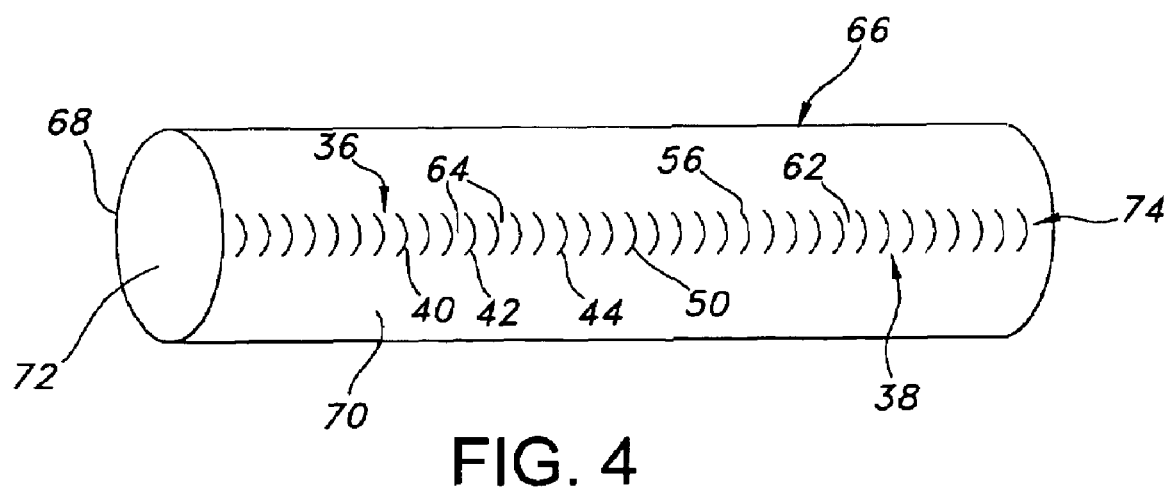
FIG. 4 is a perspective view of a tube structure formed of an ePTFE structure, a longitudinal portion of which has been micro-sintered according to the present invention.

The node and fibril micro-structure 22 of FIG. 1 is micro-sintered to produce an ePTFE structure 36 having a node and fibril micro-structure 38 in which one or more specific nodes are sintered, such as the nodes 40, 42, and the fibrils 64 are un-sintered. An ePTFE structure 36 having a micro-structure 38 which has been micro-sintered is shown in FIG. 3. The micro-structure 38 is defined by interspaced nodes 40, 42, 44, 50, 56, 62 which are interconnected by elongated fibrils 64. The entire node 62 is un-sintered. The entire node 40 is fully sintered. The fibrils 26 are un-sintered. As shown in FIG. 4, the node and fibril micro-structure 38 has specific nodes the entireties of which are fully sintered, such as the node 40, and nodes the entireties of which are partially sintered, such as the node 42. The micro-structure 38 also includes nodes the entireties of which are un-sintered, such as the node 62. The micro-structure 38 may additionally include one or more nodes each of which individually has regions which are fully sintered, partially sintered, or un-sintered. For example, the node 44 has a region 46 which is partially sintered and a region 48 which is un-sintered. The node 50 has a region 52 which is fully sintered and a region 54 which is partially sintered. The node 56 has a region 58 which is fully sintered and a region 60 which is un-sintered.

The ePTFE structure 36 may be incorporated in a tube structure 66, as shown in FIG. 4. The fibrils 64 have a longitudinal orientation 74 relative to the longitudinal axis of the tube structure 66. If the node and fibril micro-structure 38 was produced by longitudinal expansion of the tube structure 66, such longitudinal expansion also would typically result in the nodes 40, 42, 44, 50, 56, 62 having a transverse orientation relative to the longitudinal axis of the tube structure 66. The fibrils 64 have a transverse orientation relative to the longitudinal axis of the tube structure 66 if the micro-structure 38 results from radial expansion of the tube structure 66. Such radial expansion would also typically result in the nodes 40, 42, 44, 50, 56, 62 having a longitudinal or parallel relation relative to the longitudinal axis of the tube structure 66.

The nodes 40, 42, 44, 50, 56, 62 may have different transverse or radial positions relative to the outer and inner wall surfaces 32, 34 within the wall structure 30 of the tube structure 66. Also, it is possible for the specific nodes the entireties of which are fully or partially sintered or un-sintered, such as the nodes 40, 42, 62, to have a specific radial position or depth within the wall structure 68. Additionally, the location of the regions 46, 48, 52, 54, 58, 60 may correspond to a radial position or depth within the wall structure 68. For example, the specific nodes which are fully sintered, such as the node 40, may be contiguous with the outer wall surface 70 of the tube structure 66 and extend radially inward to a specific depth thereof. In such an embodiment, the fully sintered nodes may transition to and be contiguous with nodes the entireties or portions of which are partially sintered, such as the nodes 42, 44, 50, or nodes which are un-sintered, such as the node 62, at a radial position or depth between the outer and inner wall surfaces 70, 72. In some embodiments, the specific nodes, the entireties or portions of which are sintered and which are contiguous with the outer wall surface 70 may be partially sintered such as the nodes 42, 44, 50. Such partially sintered nodes may extend radially inward through the wall structure 68 to a specific depth or location between the outer and inner wall surfaces 70, 72. It is further possible for the specific nodes which are fully or partially sintered, such as the nodes 40, 42, 44, 50, 56, to extend radially entirely through the wall structure 68 from the outer to the inner wall surfaces 70, 72.

In some embodiments, the specific nodes which are fully or partially sintered, such as the nodes 40, 42, 44, 50, 56, may be contiguous with the inner wall surface 72 and may extend radially outward in a direction toward the outer wall surface 70. This outward extension of the fully or partially sintered nodes from the inner wall surface 72 may be continuous or have transitions. For example, the specific nodes which are fully or partially sintered and contiguous with the inner wall surface 72 may extend radially outward to a location which is contiguous with the outer wall surface 70. Alternatively, the specific nodes which are fully sintered, such as the nodes 40, 50, 56, and contiguous with the inner wall surface 72 may extend radially outward to a location between the inner and outer wall surfaces 72, 70. Such fully sintered nodes may further transition to partially sintered nodes, such as the nodes 42, 44, 50, at a location between the inner and outer wall surfaces 72, 70. Such partially sintered nodes may further extend radially outward to a depth or location between the inner and outer wall surfaces 72, 70 or such partially sintered nodes may extend to a location which is contiguous with the outer wall surface 70.

The nodes 40, 42, 44, 50, 56, 62 are arranged substantially longitudinally relative to the longitudinal axis of the tube structure 66, as shown in FIG. 4. The nodes 40, 42, 44, 50, 56, 62 are contained in or in close proximity to a horizontal plane of the tube structure 66. Alternatively, the nodes 40, 42, 44, 50, 56, 62 may be arranged in multiple horizontal bands to provide a striped band in which the nodes are contained thereby providing multiple regions which are strengthened by the fully or partially sintered nodes.

Figure 5:
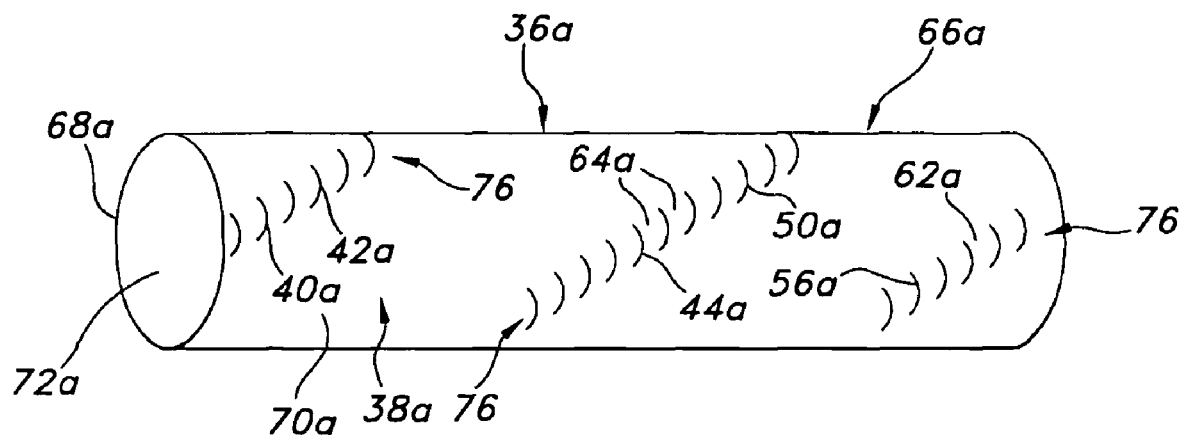
FIG. 5 is a tube structure formed of an ePTFE structure, a spiral portion of which has been micro-sintered according to the present invention.

An alternative embodiment for the tube structure 66a is shown in FIG. 5. Parts illustrated in FIG. 5 which corresponds to parts illustrated in FIG. 4 have, in FIG. 5, the same reference numeral as in FIG. 4 with the addition of the suffix "a". In this alternative embodiment, the nodes 40a, 42a, 44a, 50a, 56a, 62a have a helical orientation 76 relative to the longitudinal axis of the tube structure 66a. Such a helical orientation 76 of the nodes 40a, 42a, 44a, 50a, 56a, 62a may provide additional radial strength to the tube structure 66a.

Figure 6:
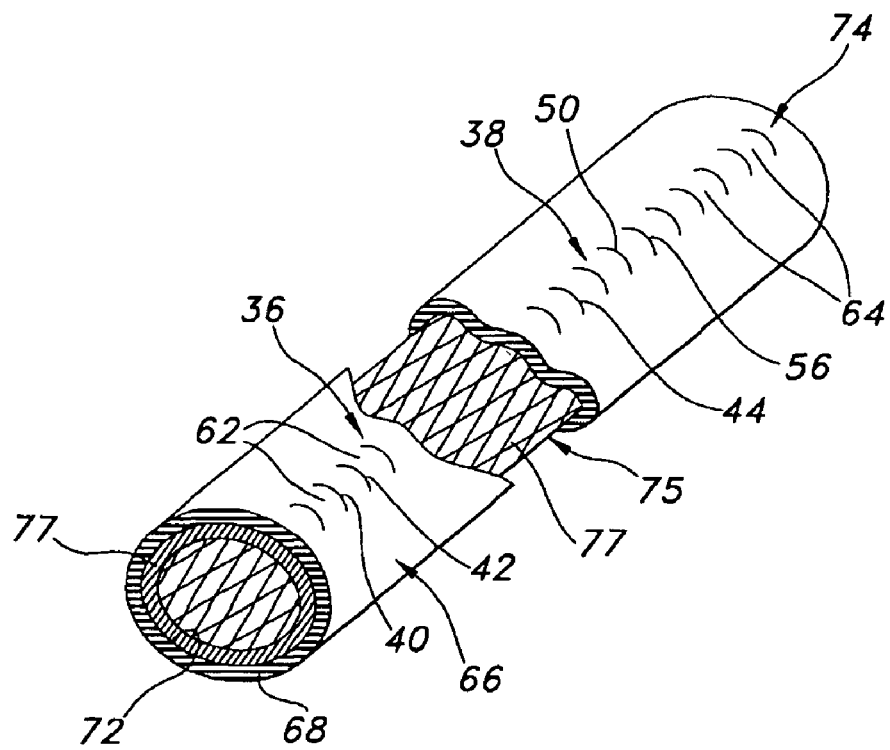
FIG. 6 is a perspective view of a tube structure corresponding to the tube structure of FIG. 4, the tube structure being assembled with a stent structure.

The ePTFE structures 20, 20a may be assembled to a stent structure 75. An embodiment of such an assembly is shown in FIG. 6, in which the ePTFE structure 20 is incorporated into a tube structure 66. The tube structure 66 is coaxially assembled with an embodiment of the stent structure 75 which is a tubular stent structure 77 such that the stent structure 77 is within the tube structure. In an alternative embodiment, the tube structure 66 may be coaxially assembled with the stent structure 77 such that the tube structure is within the stent structure. Such an alternative embodiment may be coaxially assembled further with a second tube structure 66 such that the stent structure 77 is within the second tube structure. The stent structure 77 may be assembled to the tube structure 66a in combinations corresponding to the assemblies of the tube structure 66 and stent structure 77.

The stent structure 75 may be formed of materials such as nitinol, elgiloy, stainless steel or cobalt chromium, including NP35N. Additionally, the stent structure 75 may be formed of materials such as stainless steel, platinum, gold, titanium and other biocompatible metals, as well as polymeric stents. Also, the stent structure 75 may be formed of materials including cobalt-based alloy such as Elgiloy, platinum, gold, titanium, tantalum, niobium, and combinations thereof and other biocompatible materials, as well as polymers. Additionally, the stent structure 75 may include structural members which have an inner core formed of tantalum gold, platinum, iridium, or a combination thereof, and an outer cladding of nitinol to provide composite members for improved radio-opacity or visibility. Examples of such composite members are disclosed in U.S. Patent Application Publication 2002/0035396, the entire contents of which are hereby incorporated by reference herein.

The stent structure 75 may have various embodiments. For example, the stent structure 75 may be self-expanding or expandable by a balloon. The stent structure 75 may include one or more coiled stainless steel springs, helically wound coil springs including a heat-sensitive material, or expanding stainless steel stents formed of stainless steel wire in a zig-zag pattern. The stent structure 75 may include wires which are nested, and such wires may have a zig-zag or saw-tooth pattern. The stent structure 75 may be capable of radially contracting or expanding, such as by radial or circumferential distension or deformation. Self-expanding stents include stents which mechanically urge the stent to radially expand, and stents which expand at one or more specific temperatures as a result of the memory properties of the stent material for a specific configuration. Nitinol is a material which may be included in the stent structure 75 for providing radial expansion thereof both by mechanical urging, or by the memory properties of the nitinol based on one or more specific temperatures. The stent structure 75 may include one or more of the stents disclosed in U.S. Pat. Nos. 4,503,569, 4,733,665, 4,856,516, 4,580,568, 4,732,152, and 4,886,062, the entire contents of each of which are hereby incorporated by reference herein.

The ePTFE structures 20, 20a may be treated with anti-thrombogenic agents (such as heparin, heparin derivatives, urokinase, and PPack (dextrophenylalanine proline arginine chloromethylketone)), anti-proliferative agents (such as enoxaprin, angiopeptin, or monoclonal antibodies capable of blocking smooth muscle cell proliferation, hirudin, and acetylsalicylic acid), anti-inflammatory agents (such as dexamethasone, prednisolone, corticosterone, budesonide, estrogen, sulfasalazine, and mesalamine), antineoplastic/antiproliferative/anti-miotic agents (such as paclitaxel, 5-fluorouracil, cisplatin, vinblastine, vincristine, epothilones, endostatin, angiostatin and thymidine kinase inhibitors), anesthetic agents (such as lidocaine, bupivacaine, and ropivacaine), anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick anti-platelet peptides), vascular cell growth promoters (such as growth factor inhibitors, growth factor receptor antagonists, transcriptional activators, and translational promoters), vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin), cholesterol-lowering agents, vasodilating agents, and agents which interfere with endogenous vascoactive mechanisms.

Figure 7:
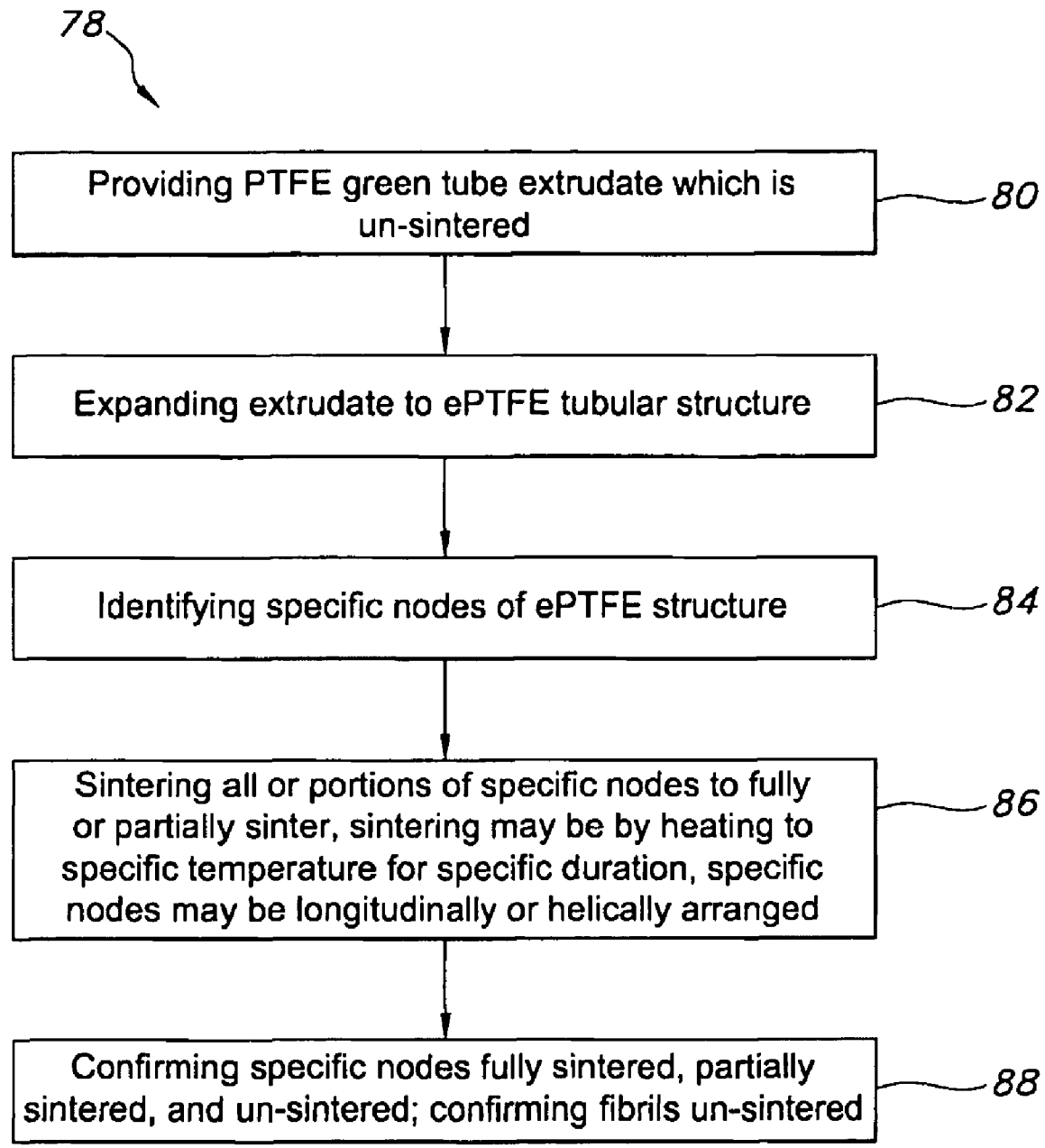
FIG. 7 is a block diagram showing a method for making an ePTFE structure of the present invention, the method including selecting and sintering specific nodes of the ePTFE structure.

A method 78 for making an ePTFE structure, such as the ePTFE structures 36, 36a, having one or more specific nodes which are fully or partially sintered is shown in FIG. 7. The method 78 provides for the making of the ePTFE structures 36, 36a which have respective tube structures 66, 66a. However, alternative embodiments of the method 78 may provide for the making of an ePTFE structure, such as the ePTFE structures 36, 36a, into a structure which is non-tubular, i.e., a sheet or other shape. The method 78 includes providing 80 a PTFE green tube extrudate which is un-sintered. The PTFE green tube extrudate is then expanded 82 to provide an ePTFE structure, such as the structures 36, 36a, which have node and fibril micro-structures 22, 38. The expansion 82 may be provided by longitudinally expanding the PTFE green tube extrudate or, alternatively, radially expanding the PTFE green tube extrudate.

Following the expansion 82, the specific nodes of the ePTFE structure, such as nodes 24, 40, 42, 44, 50, 56, 62, 40a, 42a, 44a, 50a, 56a, 62a, of the ePTFE structures 22, 38, 38a, are identified 84. The identification 84 may be provided, for example, by an electron microscope which provides sufficient magnification for the identification of specific nodes and the distinguishment thereof from the fibrils. Examples of the appearance of the nodes 24, 40, 42, 44, 50, 56, 62, 40*a*, 42*a*, 44*a*, 50*a*, 56*a*, 62*a* and fibrils 26, 64, 64*a* are shown in FIGS. 1 and 3. The nodes 24, 40, 42, 44, 50, 56, 62, 40*a*, 42*a*, 44*a*, 50*a*, 56*a*, 62*a* appear to have a larger surface area relative to the fibrils 26, 64, 64*a* which provides for the visual distinguishment of the nodes from the fibrils. Such distinguishment may be further provided by each of the nodes having many fibrils connected to a variety of locations on the outer surface of the nodes, such as the nodes 24, 40, 42, 44, 50, 56, 62, 40*a*, 42*a*, 44*a*, 50*a*, 56*a*, 62*a* and fibrils 26, 64, 64*a*. In comparison, rather than being connected to locations on the fibrils between the ends thereof, the nodes are typically connected to the ends of the fibrils. Examples of such connections are between the nodes 24, 40, 42, 44, 50, 56, 62, 40*a*, 42*a*, 44*a*, 50*a*, 56*a*, 62*a* and the fibrils 26, 64, 64*a*.

The identification 84 may alternatively be provided by a spectrometer which can identify regions of a material which have a larger density relative to other regions of material. Consequently, a spectrometer may identify the nodes, such as the nodes 24, 40, 42, 44, 50, 56, 62, 40*a*, 42*a*, 44*a*, 50*a*, 56*a*, 62*a*, since the nodes have a greater density relative to the fibrils 26, 64, 64*a*.

Following the identification 84, the specific nodes, such as the nodes 40, 42, 44, 50, 56, 40*a*, 42*a*, 44*a*, 50*a*, 56*a*, are fully or partially sintered 86. The sintering 86 may be provided by heating all or portions of the specific nodes, such as the nodes 40, 42, 44, 50, 56, 40*a*, 42*a*, 44*a*, 50*a*, 56*a* such that the heating elevates the temperatures of the specific nodes to a specific magnitude and for a time period having a specific duration. The heating which provides the sintering 86 may be applied at temperatures from about 600 degrees F. to 670 degrees F. for time durations of substantially immediately to 20 minutes. Such substantially immediate application of the heating may be provided by flash sintering which may be performed at temperatures from about 600 degrees F. to 670 degrees F. Typically, the heating which provides the sintering 86 requires a time duration which is inversely proportional to the temperature such that, for example, a shorter time duration is normally sufficient when the heating is applied at a higher temperature. The sintering 86 is sufficiently limited such that after the completion thereof, the fibrils, such as the fibrils 64, 64*a*, and some of the nodes, such as the node 62**, are un-sintered.

The sintering 86 may be directed to the entireties of one or more specific nodes, such as the nodes 40, 42, 40*a*, 42*a*, or to portions of specific nodes, such as the portions 46, 52, 54, 58 of the nodes 44, 50, 56. The sintering 86 of the portions of the nodes may be sufficient to fully sinter the portions, such as the portions 52, 58 of the nodes 50, 56. Alternatively, the sintering 86 may be sufficiently limited such that the portion of the node which is sintered is partially sintered, such as portions 46, 54 of the nodes 44, 50. Further, it is possible to sinter 86 a portion of a node such that the portion is fully sintered, such as the portion 52 of the node 50, and to sinter 86 the other portion of the node to a sufficiently limited degree such that the portion of the node is partially sintered, such as the portion 54 of the node 50. Further, the sintering 86 may be directed to an entire node such that the entire node is fully sintered, such as the node 40. Alternatively, the sintering 86 may be directed to an entire node and be sufficiently limited such that the entire node is partially sintered, such as the node 42**.

The sintering 86 may be directed to the outer wall surface of a tube structure including ePTFE, such as the outer wall surfaces 32, 70, 70*a* of the tube structures 28, 66, 66*a*. The sintering 86 may be sufficient to fully sinter the entireties or portions of the nodes which extend from the outer wall surface to the inner wall surface. Embodiments of the outer and inner wall surfaces include the outer wall surfaces 70, 70*a* and the inner wall surfaces 72, 72*a*. Embodiments of the entireties or portions of the nodes include the node 40 or portions 52, 58 of the nodes 50, 56.

Alternatively, the sintering 86 may be limited such that the entireties or portions of the nodes which are contiguous with the outer wall surface are fully sintered, and the entireties or portions of the nodes which are contiguous with the inner wall surface are partially sintered or un-sintered. Embodiments of the outer and inner wall surfaces include the outer wall surfaces 70, 70*a* and the inner wall surfaces 72, 72*a*. Embodiments of the nodes which are partially sintered and un-sintered include the nodes 40, 42 and the portions 46, 48, 54, 60 of the nodes 44, 50, 56. Embodiments of the nodes which are fully sintered include the node 40 and the portions 52, 58 of the nodes 50, 56.

In one embodiment, there is included a tube structure in which the entireties or portions of the nodes which are contiguous with the outer wall surface are fully sintered, and the nodes which are contiguous with the inner wall surface are un-sintered may have nodes the entireties or portions of which between the outer and inner wall surfaces which are partially sintered. Embodiments of the tube structure include the tube structure 66, 66*a*. Embodiments of the outer and inner wall surfaces include the outer wall surfaces 70, 70*a* and the inner wall surfaces 72, 72*a*. Embodiments of the nodes which are fully sintered include the node 40 and the portions 52, 58 of the nodes 50, 56. Embodiments of the nodes which are un-sintered include the nodes 62 and the portions 48, 60 of the nodes 44, 56. Embodiments of the nodes which are partially sintered include the node 42 and the portions 46, 54 of the nodes 44, 50**.

Alternatively, it is possible for such a tube structure to have nodes which are fully sintered and which extend radially inward from the outer wall surface such that the fully sintered nodes are contiguous with nodes which, in turn, extend to the inner wall surface. Embodiments of the tube structure include the tube structure 66, 66*a*. Embodiments of the outer and inner wall surfaces include the outer wall surfaces 70, 70*a* and the inner wall surfaces 72, 72*a*. Embodiments of the nodes which are fully sintered include the node 40 and the portions 52, 58 of the nodes 50, 56. Embodiments of the nodes which are un-sintered include the node 62 and the portions 48, 60 of the nodes 44, 56. Embodiments of the inner wall surfaces include the inner wall surfaces 72, 72*a*.

The sintering 86 may be directed to the inner wall surface, such as the inner wall surfaces 72, 72*a*, such that the entireties or portions of the nodes which are contiguous with the inner wall surface are either fully or partially sintered, such as the nodes 40, 42 or the portions 46, 52, 54, 58 of the nodes 44, 50, 56. The nodes which extend radially inward from such fully or partially sintered nodes may be nodes the entireties or portions of which are fully or partially sintered or un-sintered, such as the nodes 40, 42 or the portions 46, 52, 54, 58 of the nodes 44, 50, 56, depending upon the magnitude and duration of the sintering 86 which is directed to the inner wall surface, such as the inner wall surface 72, 72*a*. The entireties or portions of the nodes which are contiguous with the outer wall surface may be fully sintered, partially sintered or un-sintered, depending upon the magnitude and duration of the sintering 86 which is directed to the inner wall surface. Embodiments of the inner and outer wall surfaces include the inner wall surfaces 72, 72*a* and the outer wall surfaces 70, 70*a*. Embodiments of the nodes which are fully sintered, partially sintered or un-sintered include the nodes 40, 42, 62 and the portions 46, 48, 52, 54, 58, 60 of the nodes 44, 50, 56.

The sintering 86 which is directed to the outer wall surface or the inner wall surface may be selected to fully or partially sinter the entireties or portions of one or more nodes. Embodiments of the outer and inner wall surfaces include the outer wall surfaces 70, 70a and the inner wall surfaces 72, 72a. Embodiments of the nodes the entireties or portions of which are fully or partially sintered include the nodes 40, 42 and the portions 46, 52, 54, 58 of the nodes 44, 50, 56.

The sintering 86 may be directed to specific nodes, such as the nodes 40, 42, 44, 50, 56, which are arranged longitudinally relative to the tube structure 66. Alternatively, the sintering 86 may be directed to nodes, such as the nodes 40a, 42a, 44a, 50a, 56a, which are arranged helically relative to the tube structure, such as the tube structure 66a.

The sintering 86 of specific nodes, which may be considered as micro-sintering, may be provided by the selective and targeted application of heat, such as by a laser. Such heating by a laser may include magnifying the ePTFE structure 20, 36, 36a sufficiently such that the node and fibril micro-structure 22, 38, 38a can be viewed. Such heating may provide for the specific nodes to be fully or partially sintered, or un-sintered.

Alternatively, the sintering 86 of specific nodes may be provided by radiation from a heat source. Such a heat source may be provided by a high-powered microwave source, a high-power infrared source, or high-power electron dispersion.

The sintering 86 may be provided by contact heating such as by a probe. Such contact heating may require simultaneous viewing of the ePTFE structure, such as the ePTFE structures 20, 36, 36a, under suitable magnification to identify 84 the specific nodes, all or portions of which are to be fully or partially sintered. The probe is super-heated above the sinter temperature for the ePTFE structure 20, 36, 36a and applied thereto for the duration for effectuating the full or partial sintering of the nodes, such as the nodes 40, 42 and the portions 46, 52, 54, 58 of the nodes 44, 50, 56.

Alternatively, such a targeted application of heat may be provided by a scanning electron microscope which is able to direct an electron beam to one or more specific locations of the ePTFE structure, such as the ePTFE structure 20, 36, 36a.

The sintering 86 is followed by the confirming 88 of the sintering of the specific nodes, such as the nodes 40, 42, 44, 50, 56, 40a, 42a, 44a, 50a, 56a. The confirming 88 further provides for confirming that other specific nodes, such as the nodes 44, 56, 62, 44a, 56a, 62a, are un-sintered and that the fibrils, such as the fibrils 64, 64a, are un-sintered. The confirming 88 may be by visual inspection under suitable magnification such as may be provided an electron microscope. Sintering or unsintering may be confirmed 88 by the appearance of the nodes and fibrils. More specifically, sintered ePTFE appears to be opaque and cloudy while un-sintered ePTFE appears to be snow white with no light transmission.

Alternatively, the confirming 88 may be by differential scanning calorimetry (DSC) which may provide for the automation of the confirming 88. An additional alternative of the confirming 88 may include computer software which processes electronic signals regarding the sintering or un-sintering of the specific nodes and fibrils. The electronic signals which are processed by the computer software may be provided by an electron microscope. Also, the electronic signals which are processed by the computer software may be related to the density of the nodes and fibrils. The computer software and provision of the electronic signals thereto may provide for the automation of the confirming 88.

The confirming 88 of the depth or radial extent of the sintering may be provided by destructive testing such as by cross-sectionally slicing a portion of the tube structure, such as the tube structure 66, 66a, after the sintering 86 and visually examining a cross-sectional surface of the sliced tube structure.

The entire disclosure of U.S. patent application Ser. No. 11/026,657 filed Dec. 31, 2004 is hereby incorporated by reference herein. U.S. patent application Ser. No. 11/026,657 discloses embodiments of partial sintering which may be included in the sintering 86.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. An ePTFE structure having a longitudinal axis and a micro-structure comprising a plurality of specific nodes interconnected by a plurality of fibrils, the specific nodes arranged longitudinally relative to the longitudinal axis, wherein the micro-structure is microsintered in a manner such that only the specific nodes are microsintered and all of the fibrils directly connecting the specific nodes are unsintered,
    wherein each node has at least two portions, each of which has a corresponding degree of sintering, wherein said degrees of sintering are different such that each portion of the specific node has a different opacity,
    wherein each fibril has a length, the lengths of all of the fibrils directly connecting the specific nodes remaining unchanged after the specific nodes are microsintered.

2. An ePTFE structure according to claim 1, wherein one of said two portions of said specific node is fully or partially sintered.

3. An ePTFE structure according to claim 2, wherein one of said two portions of said specific node is un-sintered.

4. An ePTFE structure according to claim 1, wherein said specific nodes define first specific nodes, said ePTFE structure being tubular, said micro-structure comprising a plurality of additional specific nodes the entireties of which are fully or partially sintered, said first specific nodes and additional specific nodes being arranged longitudinally relative to the longitudinal axis of said ePTFE structure.

5. An ePTFE structure according to claim 1, wherein said ePTFE structure comprises an ePTFE tube structure.

6. An ePTFE structure according to claim 2, wherein one of said two portions of said specific node is fully sintered.

7. An ePTFE structure according to claim 2, wherein one of said two portions of said specific node is partially sintered.

* * * * *